United States Patent
O'Donoghue et al.

[19]

[11] Patent Number: 5,916,584
[45] Date of Patent: Jun. 29, 1999

[54] CONTROLLED RELEASE CONTAINER WITH CORE AND OUTER SHELL

[75] Inventors: Michael F. O'Donoghue; James A. Morris, both of Victoria, Australia

[73] Assignee: Daratech Proprietary Limited, Melbourne, Australia

[21] Appl. No.: 08/817,541

[22] PCT Filed: Oct. 25, 1995

[86] PCT No.: PCT/AU95/00707

§ 371 Date: Jun. 17, 1997

§ 102(e) Date: Jun. 17, 1997

[87] PCT Pub. No.: WO96/12466

PCT Pub. Date: May 2, 1996

[30] Foreign Application Priority Data

Oct. 25, 1994 [AU] Australia ................... PM8975

[51] Int. Cl.⁶ .................................................. A61F 2/02
[52] U.S. Cl. .................................. 424/426; 514/772.3
[58] Field of Search .......................... 424/426; 514/772.3

[56] References Cited

U.S. PATENT DOCUMENTS

| 4,450,150 | 5/1984 | Sidman ................................. 424/424 |
| 4,623,588 | 11/1986 | Nuwayser et al. ................. 428/402.24 |

FOREIGN PATENT DOCUMENTS

| 86103/91 | 2/1992 | Australia . |
| 1325209 | 8/1973 | United Kingdom . |
| 92/02211 | 2/1992 | WIPO . |
| 93/19698 | 10/1993 | WIPO . |

OTHER PUBLICATIONS

Robinson et al., "Preparation, Degradation and Performance of a Biodegradable Gentamicin Delivery System for the Treatment of Osteomyelitis," *Polymer Preprints (American Chemical Society, Division of Polymer Chemistry*, 33(2):50 (1992).

Zhang et al., "Controlled Release of Testosterone and Estadiol–17B from Biodegradable Cylinders," *Journal of Controlled Release* 29:157–161 (1994).

Marcott et al., "Delayed Release of Water Soluble Macromolecules from Polylactide Pellets," *Journal of Controlled Release*, 9:75–85 (1989).

Straw et al., "Effects of cis–Diamminedichloroplatimun II Released from D,L–Polylactic Acid Implanted Adjacent to Cortical Allografts in Dogs," *Journal of Orthopaedic Research*, 12(6):871–877 (1994).

*Primary Examiner*—Carlos A. Azpuru
*Attorney, Agent, or Firm*—Michael A. Kaufman; Flehr Hohbach Test Albritton & Herbert LLP

[57] ABSTRACT

A controlled release container includes an outer shell and a separately produced core that comprises at least one bioactive molecule. At least a portion of the outer shell comprises a biodegradable polymeric material that has a predetermined rate of degradation. The outer shell preferably is non-porous and provides a predetermined delay of at least two days from administration of the capsule before release of the active ingredient.

26 Claims, 2 Drawing Sheets

CONTROLLED RELEASE CONTAINER WITH CORE AND OUTER SHELL

This application is a 371 of PCT/AU95/00707 filed Oct. 25, 1995.

FIELD OF THE INVENTION

This invention relates to controlled release containers containing bioactive molecules as active ingredients, especially drugs or veterinary products suitable for administration to humans and other animals, in which the active ingredient is required to be administered after a predetermined time interval (delay time prior to release of the bioactive molecule) and with a release profile dependent upon the bioactive molecule being administered.

BACKGROUND OF THE INVENTION

Different active ingredients used in treatment of humans and other animals require different release profiles. For example, vaccine materials may require a pulsatile release profile subsequent to an initial delay of release, while antibiotics may require a continuous release profile subsequent to the initial delay of release. The predetermined time interval (delay time prior to release of the bioactive molecule) referred to above is dependent upon the rate of degradation of the materials and subsequent dissolution of the degradation products used for the construction of the controlled release container.

To obtain a "pulsatile" time delayed delivery system for active ingredients, it is desired that the controlled release container provide a "burst" release rather than a "continuous dribble" after the required initial time delay. Thus, containment of a bioactive molecule requires a coat or shell which remains impervious while the structure is intact but undergoing degradation.

Typical prior art methods of providing controlled release devices involve coating an active ingredient with a degradable polymer using conventional tablet coating methods. These generally involve compressing the active ingredient with an excipient and other additives into a tablet of the desired size and shape. The compressed tablet may then be coated in a pan coater by spraying with a solution or dispersion of the coating material in a solvent in an amount sufficient to give the device the required coating thickness. In an alternative coating method known as the Wurster method, the tablet is coated in a fluidised bed system.

It has been found that devices formed by these conventional techniques are most suited to short delays in release of the active ingredient. They are generally unsuitable for devices for which release of the active ingredient is desired after a longer period of, for example, about 4 to 6 weeks from administration. In addition, devices formed by conventional methods such as pan or Wurster coating, or microsphere technology, often do not provide a sufficiently well defined "burst" for administration of active ingredients such as vaccine materials.

PCT Publication No. WO 92/17165 describes a pharmaceutical or veterinary implant which is stated to release a pulse of at least one biologically active material at a controllable time interval after implantation. The implant comprises the biologically active material; an excipient comprising at least one water soluble material and at least one water insoluble material; and a polymer film coating adapted to rupture at a predetermined period of time after implantation, and wherein the excipients and polymers are biocompatible. The implants of this citation are prepared by conventional techniques from the tabletting art. Preparation methods described comprise compressing the excipients with the active ingredient into tablet-shaped solid cores using known techniques and coating with a polymer by spraying in a pan coater or a fluidised bed coater. Disadvantages with these implants is that a water insoluble non-biodegradable cage remains in the body. The implants are complicated involving complex production processes and delay times longer than about 4 weeks are difficult to achieve. The implants of this disclosure are most suited to short delays.

It is an object of the present invention to overcome or alleviate one or more of the above limitations associated with conventional controlled release devices.

SUMMARY OF THE INVENTION

According to the present invention there is provided a controlled release container comprising:

an outer shell, at least a portion of which comprises a biodegradable polymeric material having a predetermined rate of degradation; and a core enclosed by said outer shell, said core comprising at least one bioactive molecule as an active ingredient optionally admixed with one or more pharmaceutically or veterinarily acceptable carriers and/or excipients;

said portion of said outer shell preferably being non-porous, and providing a predetermined delay in the time period of release of said active ingredient.

Preferably, the polymeric material degrades when in contact with bodily fluids, this degradation comprising reduction in molecular weight of the polymeric material to a predetermined value during the predetermined delay period, wherein this degradation is sufficient to allow release the active ingredient after the predetermined delay period.

Preferably also, the polymeric material has an initial molecular weight of less than 200,000 and a molecular weight of 10,000 or less at the end of the predetermined delay period.

In another aspect, the present invention also extends to an outer shell for a controlled release container, at least a portion of said outer shell comprising a biodegradable polymeric material having a predetermined rate of degradation, said portion of said outer shell preferably being non-porous and providing a predetermined delay in the time period of release of the contents of a core enclosed by said outer shell.

It will of course be appreciated that this outer shell provides a void into which a core containing the active ingredient can be inserted.

The term "non-porous" as used herein means that the biodegradable portion of the outer shell is essentially free of any pores or micropores which might allow release of the contents of a core enclosed by the outer shell prior to degradation of the biodegradable polymeric material providing the predetermined delay in the time period of release of the contents of the outer shell.

The present invention also provides methods for the production of a controlled release container in accordance with this invention. Preferably, the outer shell of the container is formed by melt processing.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

The morphology of the biodegradable portion of the outer shell of the container of this invention is associated with the predetermined degradation profile and the associated dissolution of the degradation products which results in a predetermined delay in the time period of release of the active ingredient.

The morphology of an outer shell formed by melt processing techniques is of greater integrity with respect to lack of porosity and general uniformity than conventional coatings formed using solvent based systems such as with the pan or Wurster coaters. Such conventional coatings have difficulties associated with micro-porosity, an inherent effect which results during drying of "solvent" coating techniques. In general, the presence of micropores in the shell or coating will result in an initial dribbling of the active ingredient rather than a desired burst effect. A desirable feature of the controlled release containers of the present invention is that the need to use organic solvents associated with solvent coating techniques is avoided, and in addition the potentially adverse effects of residual solvent are removed.

Commonly used polymers may be modified to have a broad range of rates of degradation, and subsequent dissolution of the degradation products. It has also been found that by adjusting the morphology of the polymer, which is possible when using melt processing techniques, the degradation rate and subsequent dissolution of the degradation products of a known polymer may be accurately adjusted. The morphology of the outer shell may also be modified using additives such as plasticisers, nucleating agents, lubricants, processing aids, fillers, biostabilisers, and related additives, to provide control over the range of desired rates of degradation, and subsequent dissolution of the degradation products. Accordingly, the present invention extends to the use of polymeric materials which do not form crystalline regions but remain in an amorphous form.

Devices formed by conventional solvent coating methods mentioned above have a generally amorphous coating. It has been found that when the outer shell of the container of the present invention is formed by melt processing rather than conventional solvent coating techniques, it is possible to obtain the polymeric material in at least a partially crystalline form and having a defined morphology with respect to crystalline and amorphous regions. It is also possible to control the crystallinity of the polymeric material and accordingly adjust the rate of degradation of the outer shell and subsequent dissolution of the degradation products.

Although melt processing has been used in the past to form gelatine capsules, such capsules have not been used for delayed release systems. Gelatine has limited applicability as a material for a delayed release system as a result of the amorphous nature of the polymer (it has little or no ability to form a crystalline phase) and the ability to modify the gelatin, whether through blending, incorporation of additives or physico-chemical derivatization, is limited. Accordingly, the advantages of the present invention could not have been suspected from technology associated with the formation of gelatine capsules.

The outer shell of the container of this invention may be in any shape including elongate, oval, round, ball, hemispherical, capsule, rod, needle or cylinder shape. Conveniently, the shape is an elongate, cylindrical, rod or needle shape. In a most preferred embodiment, the outer shell is elongate or generally cylindrical.

In one preferred embodiment, the container of this invention is formed as an implant device. Such an implant device may comprise a single controlled release container in accordance with this invention, or it may comprise an assembly of two or more such containers, each of which may, if desired, provide a different predetermined delay in the time period of release of the active ingredient, or contain a different active ingredient.

Only a portion of the outer shell of the container of this invention may comprise the biodegradable polymeric material, and in this case the remainder of the outer shell may be non-degradable. Thus, the container may be in the form of a two-part capsule with one part being degradable and the other part either degradable at a different rate or non-degradable. In another embodiment, the container may be in the form of a capped cylinder or rod, with either the cap or the cylinder or rod being degradable and the other degradable at a different rate or non-degradable.

Preferably, however, the container of this invention is completely biodegradable, that is the outer shell entirely consists of the biodegradable polymeric material.

Preferably, the wall thickness of the outer shell of the container of this invention is about 0.25 to 1.5 mm, more preferably about 0.5 mm.

In particularly preferred embodiments of this invention, the controlled release container is provided in a generally cylindrical or capsule shape, of external dimensions of about 15–20 mm×3–4 mm for use as an implant device alone (or about 3–10 mm×3 mm for use as one part of an assembly of parts) for subcutaneous or similar delivery, or of external dimensions of about 40 mm×10 mm for use as an device for oral delivery.

Administration of the controlled release container of this invention may be by any convenient means but generally by oral ingestion or injection via the intraperitoneal, intramuscular, sub-cutaneous or intradermal route. The device may also be surgically implanted or implanted by sub-surgical procedures such as during biopsy procedures. Subcutaneous delivery of the container in the form of an implant device is particularly preferred. Where the container is to be administered by oral ingestion, particularly to ruminants, it may be incorporated into a weighed capsule or bolus or other intraruminal device, for example a device as described in International Patent Publication No. WO 93/19698 (Australian Patent Application No. 37399/93).

The bioactive molecule in the active ingredient in the core of the container may comprise any native, synthetic or recombinant pharmaceutical or veterinary agent, or food additive or supplement, including antigens, antibodies, antitoxins, nucleic acids, vaccines, cytokines, growth promotants, hormones, cancer cell inhibitory molecules or agents, immune stimulants or suppressants, anti-inflammatories, anti-microbial agents including antibiotics, anti-viral agents, anti-parasitic agent, vitamins, tonics or stimulants, minerals or inorganic or organic nutrients. The active ingredient may comprise one type of bioactive molecule or may be a mixture of different bioactive molecules.

The pharmaceutical or veterinary carriers and/or excipients may include any and all dispersion media, coatings, antibacterial, anti-fungal and/or antiviral agents and the like as well as salts such as dicalcium phosphate. Additional components which may be included are binders (e.g. gum tragacanth, acacia, corn starch or gelatin), disintegrating agent (e.g. corn starch, potato starch, alginic acid and the like) and/or a lubricant (e.g. magnesium stearate). All such components, carriers and excipients must be substantially pharmaceutically or veterinarily pure and non-toxic in the amounts employed and must be biocompatible with the bioactive molecules.

Biodegradable polymeric materials with a wide variety of compositions, properties and forms are available for use in accordance with the present invention. They are readily amenable to processing using standard melt processing technologies to give complex shapes and structures. Examples of suitable materials include the polyester family of polymers, such as the polylactide, polylactide-polyglycolide and the polyhydroxybutyrate-polyhydroxyvalerate polyesters. Other suitable polymers include polyamides such as nylon and polysaccharides, for example starch, hydrogel, cellulose acetate, hydroxypropylmethylcellulose, hydroxypropylmethylcellulose phthalate, cellulose acetate phthalate and ethyl cellulose. Polylactide-polyglycolide copolymers are particularly preferred for use in the container of this invention.

A "burst" release of the active ingredient from the controlled release container of this invention is achieved as a consequence of a bulk degradation of the biodegradable polymeric material in the outer shell. In general, the polymeric material hydrolyses in vivo so that the average molecular weight of the polymer drops over a particular period of time. Preferably, the polymeric material will have an initial molecular weight not greater than about 200,000, more preferably about 100,000, and this will then hydrolyse to an average final molecular weight of 10,000 or less, at which point the biodegradable portion of the outer shell will break up releasing substantially all the active ingredient contained in the core of the container in a pulsatile manner.

Preferably, the biodegradable polymeric material is selected so as to provide for a predetermined time delay of release of at least two days, more preferably at least four days, most preferably at least two weeks after administration.

Structural and other attributes of the polymeric material which may be adjusted to affect the rate of degradation in vitro and in vivo include copolymer composition, isomer content and molecular weight. The effect of each of these has not in the past been comprehensively studied with respect to melt processability, in combination with additive functionality, the summation of the bulk properties of the polymeric material and the subsequent degradation profiles. For example, applications reported in the literature for the pLa/pGa polyesters involve their use in solvent based applications eg. micro- and nano-sphere technology. For these applications, solubility of the polymer in the solvent for production is a primary factor determining utility.

The rate of degradation of the polymeric material may be adjusted by adjusting co-polymer composition, isomeric composition and starting molecular weight. For example, the rate of degradation of the pLa/pGa polyesters decreases with increases in the lactate, isomeric purity and molecular weight. These variables will now be discussed in more detail. The containers discussed below were formed as described in the Examples.

COPOLYMER COMPOSITION

In the following tables, the "mean degradation" is the average time of release of core (dye/lactose mixture) from a standard size implant device (19 mm×3 mm o.d.). In vitro tests were conducted at 37° C. in phosphate-buffered saline (PBS). In vivo tests were conducted in mice or sheep with the device implanted subcutaneously (in mice, under skin on back; in sheep, under skin on inside of hind leg).

For the pLa/pGa polyesters, which are illustrative of polymers which may be used in the present invention, it has been found that increasing the glycolide content of the copolymer results in a decrease in the time required for degradation both in vitro and in vivo. In Table 1 is provided data for polymer samples with or without additives. Comparable trends are observed when comparable amounts and types of additives are present in the various base polymers.

TABLE 1

| | Copolymer composition | | | | | |
|---|---|---|---|---|---|---|
| | Release time (mean days ± standard deviation) | | | Molecular Weight (Mn = after degradation) (Mw = before degradation) | | |
| | in vitro (37° C.) | mice (dye) | sheep (dye) | Mn | Mw | Dispersity |
| d,l-polylactic acid (iv = 1.0; Mw = 137,000) +5% ethyl citrate | 57 ± 5 | 69 ± 4 | 61 ± 3 | 45698 | 69699 | 1.53 |
| 75:25 d,l-polylactide-co-glycolide (iv = 0.8; Mw = 98,000) +5% ethyl citrate | 28 ± 0 | 39 ± 3 | 77 ± 17 | 48218 | 74278 | 1.54 |
| 65:35 d,l-polylactide-co-glycolide (iv = 0.6; Mw = 63,000) +5% ethyl citrate | 11 ± 1 | 9 ± 3 | 28 ± 6 | 11399 | 17689 | 1.55 |
| 75:25 d,l-polylactide-co-glycolide (iv = 0.8; Mw = 98,000) +0.5% Mg stearate | 32 ± 3 | 32 ± 5 | ND | 9342 | 31460 | 3.37 |
| 65:35 d,l-polylactide glycolide (iv = 0.6; Mw = 63,000) +0.5% Mg stearate | 20 ± 2 | 17 ± 2 | ND | 13761 | 26038 | 1.89 |
| l-polylactic acid (iv = 1.0; Mw = 102,000) | ND | 136 ± 22 | ND | 73237 | 101072 | 1.38 |
| d,l-polylactic acid (iv = 1.0; | 87 ± 10 | 121 ± 14 | 116 ± 4 | 49301 | 72776 | 1.48 |

TABLE 1-continued

| Copolymer composition | Release time (mean days ± standard deviation) | | | Molecular Weight (Mn = after degradation) (Mw = before degradation) | | |
|---|---|---|---|---|---|---|
| | in vitro (37° C.) | mice (dye) | sheep (dye) | Mn | Mw | Dispersity |
| Mw = 137,000) | | | | | | |
| 85:15 d,l-polylactide-co-glycolide (iv = 1.4; Mw = 232,000) | 41 ± 5 | 64 ± 5 | 88 ± 21 | 41808 | 90463 | 2.16 |
| 75:25 d,l-polylactide-co-glycolide (iv = 0.8: Mw = 98,000) | 30 ± 8 | 41 ± 2 | 54 ± 9 | 34451 | 53140 | 1.54 |
| Polymer Type | | | | | | |
| 75:25 d,l-polylactide-co-glycolide (iv = 0.6; Mw = 63,000) | 42 ± 2 | 58 ± 2 | ND | 34227 | 57071 | 1.67 |
| 65:35 d,l-polylactide-co-glycolide (iv = 0.6; Mw = 63,000) | 17 ± 1 | 26 ± 0 | 27 ± 10 | 17664 | 30896 | 1.75 |
| 50:50 d,l-polylactide-co-glycolide (iv = 0.8; Mw = 98,000) | 17 ± 0 | 15 ± 4 | ND | 34802 | 55656 | 1.63 |
| l-polylactic acid (iv = 1.0; Mw = 102,000) +0.5% boron nitride | 118 ± 42 | 112 ± 14 | 117 ± 3 | 15039 | 28046 | 1.87 |
| 75:25 d,l-polylactide-co-glycolide (iv = 0.8; Mw = 98,000) +0.5% boron nitride | 38 ± 3 | 46 ± 0 | 70 ± 6 | ND | ND | ND |
| 75:25 d,l-polylactide-co-glycolide (iv = 0.6; Mw = 63,000) +0.5% boron nitride | 52 ± 3 | 60 ± 6 | 53 ± 0 | 45022 | 64109 | 1.42 |
| 50:50 d,l-polylactide-co-glycotide (iv = 0.8; Mw = 98,000) +0.5% boron nitride | 12 ± 6 | 16 ± 2 | 32 ± 9 | 10744 | 17887 | 1.67 |
| 85:15 d,l-polylactide-co-glycolide (iv = 1.4; Mw = 232,000) +10% ethyl citrate | 17 ± 5 | 20 ± 3 | 24 ± 8 | 23205 | 41503 | 1.79 |
| 75:25 d,l-polylactide-co-glycolide (iv = 0.8; Mw = 98,000) +10% ethyl citrate | 20 ± 3 | 18 ± 4 | ND | 19838 | 45192 | 2.28 |
| 65:35 d,l-polylactide-co-glycolide (iv = 0.6; Mw 63,000) +10% ethyl citrate | 11 ± 1 | 9 ± 3 | 27 ± 10 | 14789 | 24047 | 1.63 |

ISOMERIC COMPOSITIONS

The proportion of different isomers present in a polymer will affect the crystallinity of the resulting polymer. Accordingly, by adjusting the proportion of isomers present in a polymer, the rate of degradation can be adjusted.

By way of exemplification the pLa/pGa polyesters will be discussed. Naturally occurring lactic acid is an optically pure molecule. It is also possible to obtain a racemic mixture of lactide monomer via chemical synthesis. As a result the polylactides are available as either enantiomerically pure or racemic polymer. The racemic d,I-pLa is amorphous whereas the optically pure I-pLa is a highly crystalline material. I-pLa degrades slowly both in vitro and in vivo.

In Table 2 is illustrated a comparison of the degradation rate of d,I-pLa and I-pLa as the neat polymer and with additives.

The mechanism for the difference in the rate of degradation of the d,I- and I-lactide polymers is thought to be predominantly physical rather than chemical in nature. For crystalline materials (I-pLa), water entry is retarded as a result of the packing of the matrix. Amorphous materials (d,I-pLa), on the other hand, have a relatively open matrix allowing relatively free passage of water into the bulk of the polymer.

This crystallinity is a useful parameter for control of the degradation rate. The use of additives, for example, plasticisers such as ethyl citrate or diisooctyl phthalate plus nucleating agents such as boron nitride, and internal lubricants such as magnesium and zinc stearate, affects the degree and distribution of crystallinity and in conjunction with control of molecular weight, allows control of the degradation profile.

TABLE 2

Isomer composition effects

| Polymer Composition | Release time (Mean days ± standard deviation) | | | Molecular Weight | | |
|---|---|---|---|---|---|---|
| | in vitro (37° C.) | mice (dye) | sheep (dye) | Mn | Mw | Dispersity |
| d,l-polylactic acid (iv = 1.0; Mw = 137,000) | 87 ± 10 | 121 ± 14 | 116 ± 4 | 49301 | 72776 | 1.48 |
| l-polylactic acid (iv = 1.0; Mw = 102,000) | ND | 136 ± 22 | ND | 73237 | 101072 | 1.38 |
| d,l-polylactic acid (iv = 1.0; Mw = 137,000) +10% ethyl citrate +0.5% boron nitride | 74 ± 4 | 76 ± 5 | 97 ± 7 | 71077 | 104247 | 1.47 |
| l-polylactic acid (iv = 1.0; Mw = 102,000) +0.5% boron nitride +10% ethyl citrate | 66 ± 29 | 99 ± 15 | ND | 29922 | 46982 | 1.57 |

STARTING MOLECULAR WEIGHT

Data indicating the effect of starting molecular weight on the degradation profile are provided in Table 2. In general, the higher the starting molecular weight for a given material the longer the period for degradation.

MOULDING CONDITIONS

Examples of suitable techniques for melt extrusion to produce continuous tubing and injection moulding for the production of capsules follow. The results in Table 3 are illustrative of the differences in degradation outcomes obtained from the processes of melt extrusion to produce continuous tubing and injection moulding for the production of capsules. It can be seen in the examples that the difference in delay of release between 50:50 pLa/pGa extruded tubing and injection moulded capsules was 30 compared to 15 days.

The difference in delay of release between extruded tubing and injection moulded capsules is due to degradation which occurs during production of the injection moulded samples which results in the molecular weight of the injection moulded samples falling. Little or no degradation of molecular weight results during extrusion processing.

It has been found that a consistent degree of degradation is obtained upon repeated processing of the same materials under the same conditions during the injection moulding process and accordingly selection of the process is an additional parameter by which the morphology of the outer shell may be adjusted to adjust the rate of degradation of the outer shell.

The equipment used for processing the polymers also has an effect on the physiochemical properties of the container and affects the rate of degradation. As noted above, melt extrusion has little effect on the polymers with respect to molecular weight whereas injection moulding has a significant effect with degradation levels of the order of 30 to 50% being observed in some instances.

The design of the moulding equipment also has an effect. For example, injection moulded capsules have been produced by a "Ram" based injection moulder, the Butler 10/60 and by a screw based injection moulder, a Boy. Both induce significant degradation during processing although to different levels, about 75% for a Ram based injection moulder compared with 50% for a screw based injection moulder. The reason for this is that the screw injection moulder is able to force feed the polymer into the moulding tool using the power of the screw enabling processing of materials at lower temperatures, thus inducing less thermal degradation. Accordingly, selection of the moulding equipment enables the rate of degradation of the outer shell to be adjusted.

Extruded tubing vs injection moulding

| Polymer Type | Mean Degradation Time (Days) | |
|---|---|---|
| | in vitro samples (37° C.) | in vivo samples mice (Dye) |
| Extruded Tubing Samples | | |
| 50:50 d,l-polylactide-co-glycolide (i.v. = 0.8; MW = 98,000) | 29 | 31 |
| 50:50 d,l-polylactide-co-glycolide (i.v. = 0.8; MW = 98,000) +0.5% boron nitride | 31 | 31 |
| d,l-polylactic acid (i.v. = 1.0; MW = 137,000) +0.5% boron nitride +0.5% ethyl citrate | 150 | |
| Injection Moulded Samples | | |
| 50:50 d,l-polylactide-co-glycolide (i.v. = 0.8; MW = 98,000) | 17 | 15 |
| 50:50 d,l-polylactide-co-glycolide (i.v. = 0.8; MW = 98,000) +0.5% boron nitride | 19 | 16 |
| d,l-polylactic acid (i.v. = 1.0; MW = 137,000) +0.5% boron nitride +0.5% ethyl citrate | 94 | 95 |

γ-IRRADIATION

γ-irradiation increases the rate of degradation of the polymeric material, and may decrease the degradation time by about 25%.

The presence of additives in the polymer matrix may reduce the time required for degradation and may be, for example, about 20% compared to 25% for polymers not containing additives. The presence of more than one additive may have a synergistic effect, for example, the presence of ethyl citrate and boron nitride may reduce the degradation time more than would be expected on the basis of summation of the additive effect.

Results of the effect of y-irradiation on the degradation profile of different polymer compositions are provided in Table 4.

| Polymer Type | Irradiation effects | | |
|---|---|---|---|
| | Mean Degradation Time (Days) | | |
| | in vitro samples (37° C.) | in vivo samples mice (Dye) | irradiation kGy |
| Extruded Tubing Samples | | | |
| 75:15 d,l-polylactide-co-glycolide (i.v. = 0.6; MW = 63,000) | 93 | — | 0 |
| | 56 | — | 25 |
| | 104 | 76 | 0 |
| | 65 | 61 | 25 |
| 75:25 d,l-polylactide-co-glycolide (i.v. = 0.6; MW = 63,000) +0.5% ethyl citrate | 69 | 84 | 0 |
| | 56 | 64 | 25 |
| 75:25 d,l-polylactide-co-glycolide (i.v. = 0.8; MW = 98,000) | 114 | — | 0 |
| | 45 | — | 25 |
| 85:15 d,l-polylactide-co-glycolide (i.v. = 1.4; MW = 232,000) | 62 | | 0 |
| | 50 | | 25 |
| d,l-polylactic acid (i.v. = 1.0; MW = 137,000) | 138 | | 0 |
| | 122 | | 25 |
| d,l-polylactic acid | 149 | 164 | 0 |

-continued

| Polymer Type | Irradiation effects | | |
|---|---|---|---|
| | Mean Degradation Time (Days) | | |
| | in vitro samples (37° C.) | in vivo samples mice (Dye) | irradiation kGy |
| (i.v. = 1.0; MW = 137,000) | 116 | 104 | 25 |
| +0.5% ethyl citrate | | | |
| d,l-polylactic acid | 153 | 123 | 0 |
| (i.v. = 1.0; MW = 137,000) | 113 | >266 | 25 |
| +0.5% boron nitride | | | |
| d,l-polylactic acid | 150 | >266 | 0 |
| (i.v. = 1.0; MW = 137,000) | 104 | >266 | 25 |
| +0.5% boron nitride | | | |
| +0.5% ethyl citrate | | | |

PLASTICISER EFFECTS

The addition of plasticiser to the polymer material decreases the time of delay in the period of release of the active ingredient. The effect of plasticiser on the degradation profiles of polymers is illustrated in Table 5. It is postulated that the effect of the plasticiser is as a result of the decreased amorphous polymer material density. It is preferred that the level of added plasticiser is above about 0.5%. If the level of added plasticiser is less than 0.5%, there may be insufficient plasticiser necessary to induce an effect on the degradation profile.

TABLE 5

| | Plasticiser effects | | | | | |
|---|---|---|---|---|---|---|
| | Release Time (mean days ± standard deviation) | | | Molecular weight | | |
| Polymer Type | in vitro (37° C.) | mice (dye) | sheep (dye) | Mn | Mw | Dispersity |
| d,l-polylactic acid (i.v = 1.0; Mw = 137,000) | 87 ± 10 | 121 ± 14 | 116 ± 4 | 49301 | 72776 | 1.48 |
| +0.5% ethyl citrate | 92 ± 11 | 88 ± 11 | 96 ± 7 | 43382 | 94615 | 2.18 |
| +2.5% ethyl citrate | 55 ± 9 | 75 ± 2 | ND | 28306 | 62045 | 2.19 |
| +5% ethyl citrate | 57 ± 5 | 69 ± 4 | 61 ± 3 | 45698 | 69699 | 1.53 |
| +10% ethyl citrate | 74 ± 4 | 76 ± 5 | 97 ± 7 | 71077 | 104247 | 1.47 |
| 85:15 d,l-polylactide-co-glycolide (iv = 1.4; Mw = 232,000) | 41 ± 5 | 64 ± 5 | 88 ± 21 | 41808 | 90463 | 2.16 |
| +5% ethyl citrate | 22 ± 4 | 29 ± 3 | 14 ± 0 | 17237 | 341444 | 1.98 |
| +10% ethyl citrate | 17 ± 5 | 20 ± 3 | 24 ± 8 | 23205 | 41503 | 1.79 |
| 75:25 d,l-polylactide-co-glycolide (iv = 0.8; Mw = 98,000) | 30 ± 8 | 41 ± 2 | 54 ± 9 | 34451 | 53140 | 1.54 |
| +5% ethyl citrate | 28 ± 0 | 39 ± 3 | 77 ± 17 | 48218 | 74278 | 1.54 |
| +10% ethyl citrate | 20 ± 3 | 18 ± 4 | ND | 19838 | 45192 | 2.28 |
| +15% ethyl citrate | ND | ND | ND | 17140 | 46453 | 2.71 |
| 65:35 d,l-polylactide-co-glycolide (iv = 0.6; Mw = 63,000 | 17 ± 1 | 26 ± 0 | 27 ± 10 | 17664 | 30896 | 1.75 |
| +5% ethyl citrate | 11 ± 1 | 9 ± 3 | 28 ± 6 | 11399 | 17689 | 1.55 |
| +10% ethyl citrate | 11 ± 1 | 9 ± 3 | 27 ± 10 | 14789 | 24013 | 1.68 |

As discussed above, the present invention provides a controlled release container having a predicted rate of degradation and subsequent dissolution of the degradation products providing a defined delay in the time period of release of the active ingredients.

The following Table 6 illustrates specific delay times which may be achieved by adjusting the morphology of the outer shell.

TABLE 6

| Delay Time (days) | Composition of Outer Coating |
|---|---|
| 15 | 50:50 d,l-pLa/pGa |
| 20 | 65:35 d,l-pLa/pGa |
| 50 | 75:25 d,l-pLa/pGa |
| 70 | 85:15 d,l-pLa/pGa |
| 100 | d,l-pLa |

The degradation time may be further refined by adjusting the starting molecular weight and level and type of additive.

In a preferred method of forming the containers of the present invention, heat and/or pressure is applied to polymeric materials to convert the polymer to a fluid state. Once in a fluid state the polymer may be shaped to form the outer shell by moulding and the shape maintained by cooling to below the flow temperature of the polymer. This has the added advantage that the size and shape of the outer shell of the container may be controlled. No additives such as solvent are present which will require removal, avoiding porosity of the outer shell. Where solvent removal from a coating material is required, a porous coating generally results.

Some of the additional advantages of controlled release containers which have been formed by melt processing include:

uniformity of shape (the mould design determines the size and shape of the product);

ease of quality control through (a) control of addition of various agents, (b) control over the product shape, (c) control over the processing conditions, etc.;

no requirement for removal of materials used in the production process (such as solvents in the solvent coating processes indicated above);

applicability to a wide range of polymeric materials and blends of various materials;

simplicity of processing; and flexibility in design and manufacture, e.g. use of multiple components using the same or different materials for construction of each part.

In a preferred form, the entire outer coating is composed of a biodegradable polymeric material. A container may be formed in two (or three or more) parts by injection moulding such that the parts may be joined to form a sealed container. During assembly of the parts of the container a core is placed inside before assembly of the components and may be sealed using any suitable means such as glue, friction or a self locking screw design or by welding with ultrasonic technology.

The entire outer shell or part only of the outer shell of the controlled release container may be made of the biodegradable polymeric material with defined degradation and dissolution rates. The remainder of the outer shell of the container may be prepared from a tough non-biodegradable or very slowly degrading or even photo-degradable polymeric material. Such devices may be useful for application to the sub-cutaneous, intradermal, intramuscular, intraperitoneal and ruminal delivery of bioactive molecules where the size of the container and accordingly the cost of containing the active ingredient within a biodegradable material may be relatively significant. For example, the container may comprise a sleeve which is composed of biodegradable materials and the remainder of the body of the container composed of an alternate material.

The core formulation may also be adjusted to assist in attainment of the burst effect required for pulsatile delivery. For example, the use of osmotic modifiers to swell the active ingredient and thus cause a burst as soon as the biodegradable portion of the outer shell of the container reaches a critical stage of weakness. Alternatively, for continuous or sustained release of the active ingredient from the container subsequent to biodegradation of the outer shell, i.e. subsequent to the time interval of delay of release, excipients in the core may be used which inhibit the rapid release and result in a "dribble" effect and thus a sustained release profile is obtained after the initial delay.

In another aspect, the present invention provides a method of administering an active ingredient to a human or animal in a controlled release regime by administering to the human or animal a container as described above.

The recipient of the container may be a human, livestock animal, eg. a sheep, cow, horse, pig, goat or donkey, poultry, eg. chicken, turkey, goose or game bird, a laboratory test animal, eg. a rabbit, guinea pig, rat or mouse, companion animal, eg. dog or cat or a wild animal in the captive or free state.

As previously described, administration of the container may be by any convenient means such as by oral ingestion or by injection via the intraperitoneal, intramuscular, subcutaneous or intradermal route.

The amount of active ingredient used in a container will vary depending on the type of active ingredient, condition in the animal being treated and the presence or absence of agonists to the active ingredient or antagonists to the condition being treated. In general, an effective amount of an active ingredient is employed meaning an amount effective to induce, stimulate, promote or otherwise initiate the immediately intended result. For example, if the active ingredient is an antigen, the effective amount is that required to stimulate an immune response to the antigen. Commonly, the active ingredient will be present in amounts ranging from a few micrograms to gram quantities per container.

BRIEF DESCRIPTION OF THE DRAWINGS

The invention will be further described by reference to the following non-limiting Figures and Examples. In the Figures.

Figure 1:
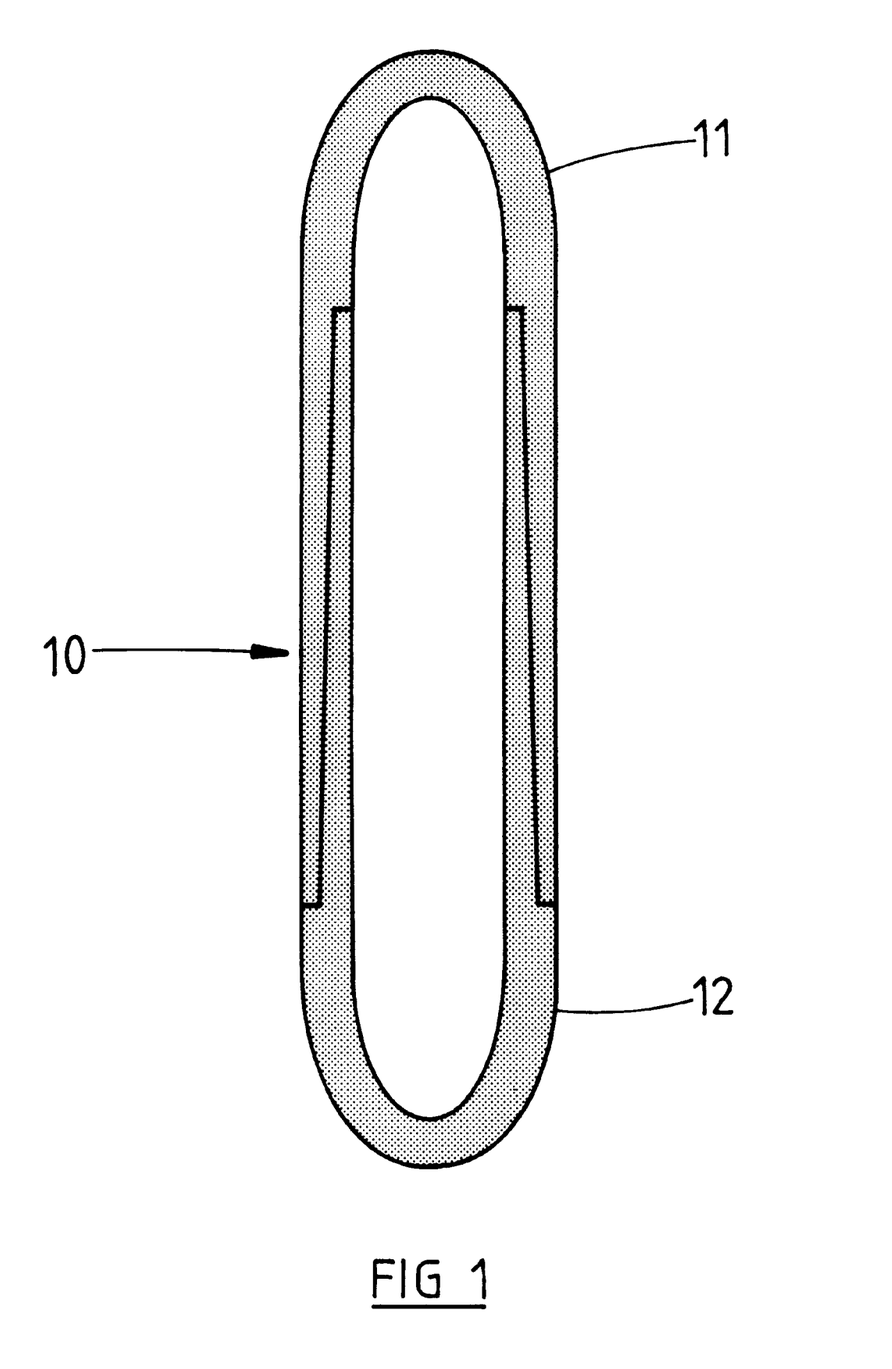
FIG. 1 is a schematic cross section of a container of the present invention.
Figure 2:
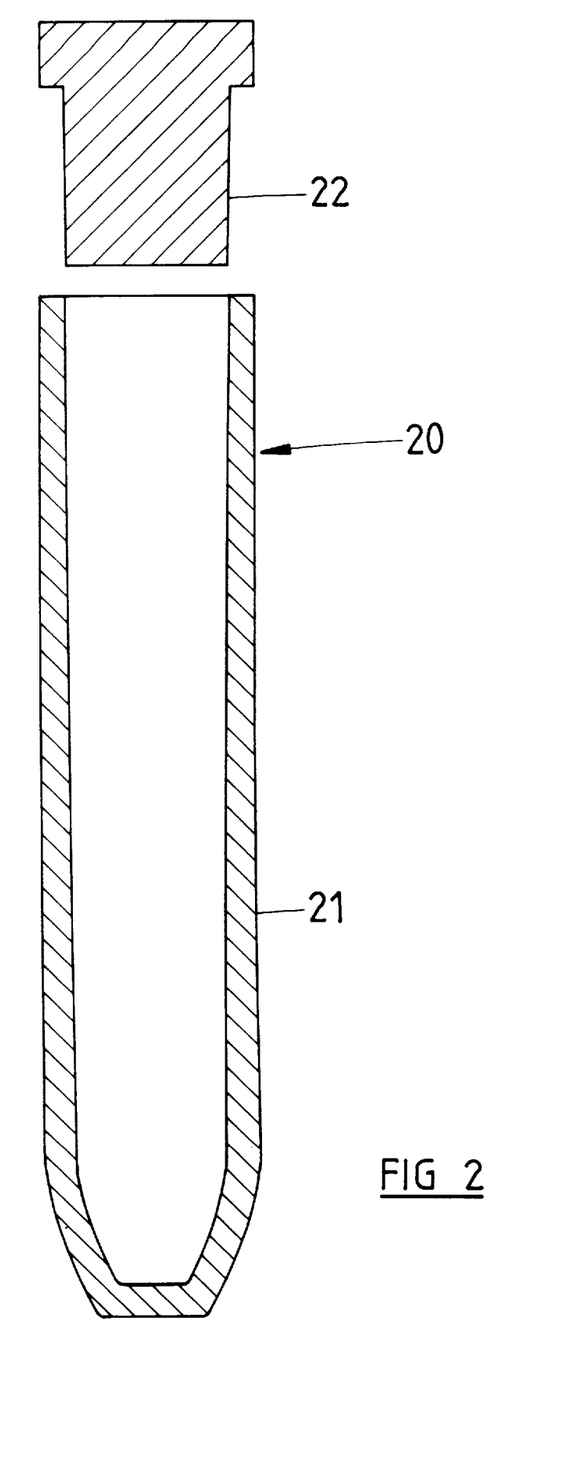
FIG. 2 is a schematic cross section of a further embodiment of a container of the invention.

Container 10 shown in FIG. 1 has a two-part outer shell for a capsule or implant, for example having outer dimensions 15.5 mm×3.5 mm and wall thickness of 0.5 mm. The outer shell consists of parts 11 and 12, either or both of which may be formed from biodegradable polymeric material, which are shaped to sealingly fit together after a core containing active ingredient has been inserted into the outer shell. Container 20 shown in FIG. 2 similarly has a two-part outer shell forming an implant device, for example having outer dimensions of about 19 mm×3.5 mm and a wall thickness of 0.5 mm. Container 20 consists of tubular implant body 21 to house a core containing active ingredient and a cap 22 which seals the implant body 21. Once again, either or both of the implant body 21 or the cap 22 may be formed from biodegradable polymeric material.

EXAMPLES

Example 1

Melt Processability of Materials

The processing of the polymers involved in this investigation involved two separate stages. These consisted of compounding and extrusion (treated as a single process), and secondly injection moulding. Each of these processes can have a detrimental effect on the polymer due to thermal and shear degradation. A large part of this work was directed towards understanding how the polymers of interest were affected by these factors and the most effective ways to minimise these effects. In addition, the effect of various additives, e.g. plasticisers and internal lubricants on the molecular weight of the final capsules was studied in anticipation that the degradation of the polymer may be modified by the inclusion of these compounds.

1. Compounding and Extrusion.

The compounding of additives and plasticisers into the polymers was performed on a Brabender Extruder fitted with either a single or twin screw extruder. Initial work to produce tubing was performed using a cross head attached to the single screw extruder. The single screw was also used to compound some of the earlier blends but later work used the twin screw which was quicker and the materials generally fed more easily. The process was basically the same for both extruders, with the only differences being:

torque settings the single screw requires harder stuffing (into the feed throat) of some materials the twin screw requires juggling of two polymer strands into the pelletiser more loss associated with the twin screw extruder.

Extrusion Conditions.

Extruder temperatures were very dependent on the polymer in use and on additives present. Table 7 summarises some of the conditions used for the poly-I lactide (pLa) and polylactide/polyglycolide (pLa/Ga) polymers, with zone temperatures of 90–130° C. and die temperatures of generally 120–140° C. (high MW or crystalline materials, e.g. L210, L214, which had melting points of ~185° C., required zone temperatures of 210–250° C., and die temperatures of 235–275° C.).

TABLE 7

Brabender extruder conditions.

| Polymer | MW. | ID | Melt ° C. | Zone 1° C. | Zone 2° C. | Zone 3° C. | Die ° C. | rpm | screw |
|---|---|---|---|---|---|---|---|---|---|
| l-pLa | 2000 | L104 | 132 | 85 | 95 | 115 | 120 | 15 | single |
| l-pLa | 102k | L206 | 183 | 190 | 185 | 185 | 185 | 20 | single |
| l-pLa | 629k | L210 | 235 | 195 | 210 | 225 | 235 | 20 | single |
| l-pLa | | L214 | >255 | 210 | 235 | 250 | 275 | 20 | single |
| dl-pLa | 137k | R206 | 140 | 90 | 110 | 125 | 135 | 20 | single |
| +0.5% MgSt | | | | 90 | 110 | 125 | 130 | 25 | twin |
| +1% MgSt | | | | 90 | 110 | 125 | 130 | 25 | twin |
| +0.5% ZnSt | | | | 90 | 110 | 125 | 135 | 25 | twin |
| +1% ZnSt | | | | 90 | 110 | 125 | 135 | 25 | twin |
| p-Ga | | G205 | 192 | | | | | | |
| pLa/Ga (65:35) | | | | 100 | 120 | 120 | 140 | 20 | twin |
| pLa/Ga (75:25) | 63k | RG755 | 127 | 130 | 130 | 140 | 130 | 20 | twin |
| pLa/Ga (75:25) | 98k | RG756 | 135 | 130 | 130 | 140 | 130 | 16 | twin |
| +5% EC | | | | 90 | 110 | 125 | 130 | 20 | twin |
| pLa/Ga (85:15) | 232k | RG858 | 150 | 135 | 155 | 160 | 180 | 20 | single |
| pLa/Ga (50:50) | 98k | R506 | | | | | | | |

Degradation of polymer during extrusion.

A series of repeated Brabender extrusions in which polymer samples were subjected to 2, 4, 6 and 8 extrusion cycles was completed on DL-pLa (R206) and DL-pLa/Ga 75:25 (RG756) to determine the extent of degradation that is caused by excessive processing.

In the case of polymer DL-pLa (R206), as shown in the following Table 8, multiple passes through the Brabender have very little effect on the molecular weight of the polymer extrusion, dropping from 99084 (nom. 137000) to 96163 after 8 passes. Subsequent processing through the Butler injection moulder has a much greater effect; two passes through the Brabender, followed by injection moulding to form capsules resulted in a 30% drop in polymer MW from 99084 (MW) to 69699 MW). A further two cycles reduced it to 49186, representing a 50% reduction from the initial figure.

Additional 2 or 4 cycles did not appear to reduce the MW any further although the figures are inconsistent. For the polymer DL-pLa/Ga 75:25 (RG756), again multiple cycles through the Brabender reduced the molecular weight from 93323 to 82701 after 2 passes, a drop of 12%, and down to 73782 after 8 passes, a drop of approximately 25%. When capsules were moulded from these extruded polymers much more significant reductions were recorded. Moulding after 4, 6 and 8 Brabender passes decreased the polymer to 48%, 51% and 37% of its original MW.

TABLE 8

Effect of Brabender cycles and injection moulding on polymer MW.

| Polymer | Brabender passes | Initial MW | MW (pellets) | MW (capsules) |
|---|---|---|---|---|
| DL-pLa (R206) | 2 | (137000) | 99084 | 69699 |
|  | 4 |  | 96953 | 49186 |
|  | 6 |  | 98791 | 58543 |
|  | 8 |  | 96163 | 44313 |
| DL-pLa/Ga 75:25 (RG756) | 2 | (93323) | 87201 | n.a. |
|  | 4 |  | 78080 | 45300 |
|  | 6 |  | 78128 | 48721 |
|  | 8 |  | 73782 | 34451 |

2. Injection Moulding.

The technique for injection moulding the polymers and polymer blends using a Butler 10/60 Injection Moulding machine follows the same principles as moulding conventional polymers. The polymers degrade readily when thermally processed and not having a stable environment (temperature, humidity, etc.), the operation has required in-process optimisation for each polymer blend. The automatic moulding cycle, including the operation of the four cavity capsule and lid moulding tool is as follows:

1. Insert moulding pins into capsule cavity in tool.
2. Close mould.
3. Position sprue puller pin on tool.
4. Inject polymer into mould.
5. Allow polymer to cool.
6. Retract moulding pins from capsule cavity in tool.
7. Open tool, retract sprue puller pin after tool opens but before ejector plate is actuated.
8. Blow ejected moulding clear of tool.

Cycle times and moulding conditions.

The total cycle time of 10–20 seconds for the injection moulding process is dependent on the above operations. The main contributors to the cycle time being:

close mould 1 sec.
inject polymer 3–10 sec.
cool 5–10 sec.
open mould 1–2 sec.

The cycle time for this process varies considerably depending on the individual polymer or polymer blend characteristics. Polymer injection time, as mentioned above, can vary between 3–10 seconds and is largely determined by the melt viscosity of the polymer. This is further dependent on polymer melt temperature, and MW of the polymer. The following Table 9 gives an indication of the conditions used in the injection moulding of the polymers.

TABLE 9

Typical temperature settings for injection moulding.

|  | Feed zone | Main heat zone | Die temp. |
|---|---|---|---|
| amorphous polymer, eg R206, RG756, RG705 | 100–110° C. | 145° C. | 40–45° C. |
| crystalline polymer, eg L206, L210, L214 | 170 | 185 | 55–60 |

Example 2

Repeatability and Reproducability Studies

The initial experiment, involving 500 mice and 100 sheep and implants was composed of the d,I-pLa R206, (samples LC, LD, LE, LF and LG). In this experiment, 5 batches of the same polymer (dI,-pLa, i.v.=1.0) plus additives (0.5% ethyl citrate and 0.5% boron nitride) were prepared (Brabender extrusion) and then injection moulded as individual batches. Samples for evaluation, both in vitro and in vivo, were collected subsequent to the run having "settled" to a constant state of degradation.

The data from the experiment indicate:

intra-group variability (repeatability);

inter-group variation (reproducability); and a lack of species specificity for in vivo degradation.

Overall, the data collected indicate good repeatability and reproducability with minimal species-to-species variation. The physico-chemical datas (thermal and molecular weight analysis) collected from samples of implants from different positions, within the same run and from the 5 different production batches indicated that the samples were, nominally, identical in form and structure.

Intra-run repeatability.

Capsules from batches of the run were separated into groups of 10 as they were moulded. Comparison of the available data from these batches indicates a random distribution of release of dye with respect to time and position within the run for each set of data.

The conclusion from these data is that the intra-run distribution of release is random and that the repeatability of the samples from this experiment has been sufficient to prove the adequacy of the technology.

Inter-run reproducability.

The second objective of this experiment was to ascertain the ability to prepare implants with comparable properties, physico-chemical and physiological, on a batch to batch basis. To evaluate the variability 5 separate batches of implants were prepared. The data was collected as a cumulative number of releases for each implant group against time for each of the runs in vitro and in both mice and sheep.

The collected data indicated the following:

the trend of releases is comparable for the groups;

there have been no failures (releases within 14 days of implantation); and there have been very few early releases (1% released prior to 70 days).

The data also indicate the following with respect to inter-run repeatability;

the trend within groups is comparable between groups (for both species);

the variability within groups, as measured by the standard deviation, is comparable between groups (for both species);

with the mice, 4 of the 5 batches have exhibited comparable mean and standard deviation; and the 5 batches in sheep have shown good reproducability.

Example 3

Delayed Pulsed Release of a Vaccine

The subcutaneous implant delayed release delivery system of this invention was used to deliver *Pasteurella multocida* antigen to mice. Four groups of 50 animals were used. The four groups consisted of:

| | |
|---|---|
| Group 1 Non-vaccinated controls | no antigen; |
| Group 2 Vaccinated controls | liquid priming dose only; |
| Group 3 Vaccinated controls | liquid priming dose only delivered by the delayed release system; |
| Group 4 Vaccinated test group | liquid priming dose plus booster dose delivered by the delayed release system. |

Mice in Group 1 were administered with a subcutaneous implant containing only an inert marker (methylene blue) at day zero. This group served the purpose of being both the negative control group and the indicator group for determination of the time of release of the antigen.

Mice in Group 2 were administered, by subcutaneous injection, a liquid priming dose of the antigen formulation on day zero. No booster dose was given to animals in this group.

Mice in Group 3 were administered, at day zero, with a priming dose of the antigen formulation within the delayed release implant delivery system. No booster dose was given to animals in this group.

Mice in Group 4 were administered, by subcutaneous injection, a liquid priming dose of the antigen formulation at day zero followed by a booster dose of the antigen formulation within the delayed release delivery system, also administered at day zero.

The antibody levels of all mice were monitored by Enzyme Linked Immunosorbent Assay (ELISA) for 47 days. At day 52, the mice were challenged with live *Pasteurella multocida* (approximately $5 \times 10^5$ organisms/mouse). Mice were monitored for survival and blood antibody levels (by ELISA) for a further 30 days (not all data presented). The results are presented in Table 10.

TABLE 10

Response to Pasteurella antigen

| Group # | Time for Administration (days) | | | | |
|---|---|---|---|---|---|
| | 0 | 16 | 33 | 47 | 53 |
| | | % Seroconversion | | | % Survival |
| 1 | 0 | 2 | 7 | 9 | 0 |
| 2 | 0 | 0 | 22 | 29 | 18 |
| 3 | 0 | 7 | 24 | 41 | 18 |
| 4 | 0 | 7 | 70 | 90 | 58 |

The mean delay time for the materials used in production of this specific delayed release delivery system was 18 days with a standard deviation of three days (based on release of an inert marker in the Group 1). Less than 10% of mice in Group 1 gave a positive ELISA result over the time of the experiment. None of the mice in this control group survived the challenge with the live organisms.

In Group 2, seroconversion was observed in 22% of the mice at 33 days after immunisation. 18% of the animals in this control group survived the challenge with the live organisms.

Mice in Group 3 showed seroconversion in 24% of the animals 33 days after immunisation. This compares with the results obtained for Group 2. 18% of the animals in Group 3 survived challenge.

70% of mice in Group 4 had seroconverted at 33 days. 58% of the animals in this control group survived the challenge.

Example 4

Delayed Pulsed Release of Anthelmintic from an Intraruminal Bolus

Abamectins and ivermectins are macrolide antibiotics well known for their use in livestock as antiparasitic or anthelmintic agents. In particular, use against nematode worms and endoparasites and ectoparasites has been a specific area of application. Prolonged exposure of the parasites to anthelmintics, often at sublethal doses, has resulted in selection of resistant parasites. Adverse environmental consequences have also arisen. The effectiveness of application of these anthelmintics could be extended by delayed release, the most preferred delivery system being one that can produce a pulsed release at periodic intervals subsequent to administration.

The delayed release delivery system of this invention was used to deliver an anthelmintic orally to cattle. Five Hereford heifers, approximately 2 years of age, were administered a bolus by a commercial balling gun. The bolus contained a test formulation of the anthelmintic in a device that fitted tightly within the cage portion of the bolus device. The five animals selected had moderate gastrointestinal nematode egg counts of 180 to 300 eggs per gram (epg) of faeces. Faecal samples were collected before treatment (day zero) and periodically after treatment to monitor changes in faecal egg counts.

A modified McMaster technique was used to estimate faecal egg counts. Faeces (4 gm) were mixed with 60 ml saturated NaCl (SG 1.16). When 1 chamber (0.5 ml) of the McMaster slide was counted, sensitivity was 30 epg; if 2 chambers were counted, it increased to 15 epg. Observed Faecal Egg Counts (FEC) are presented in Table 11.

TABLE 11

Nematode Faecal Egg Counts recorded in calves following administration of intraruminal bolus containing an anthelmintic.

| | Days after bolus device was administered | | | | | | | | | |
|---|---|---|---|---|---|---|---|---|---|---|
| Calf # | 0 | 3 | 6 | 9 | 12 | 17 | 21 | 25 | 28 | 35 |
| 746 | 240 | 105 | 450 | 135 | 240 | 0 | 0 | 0 | 0 | 0 |
| 747 | 285 | 90 | 750 | 285 | 450 | 390 | 930 | 30 | 0 | 0 |
| 748 | 300 | 255 | 990 | 45 | 30 | 15 | 30 | 0 | 0 | 0 |
| 749 | 390 | 195 | 510 | 225 | 135 | 510 | 30 | 0 | 0 | 0 |
| 750 | 180 | 300 | 690 | 525 | 330 | 150 | 780 | 180 | 525 | 0 |
| Mean= | 290 | 250 | 730 | 265 | 165 | 225 | 280 | 42 | 105 | 0 |

Between days zero and 12, all five calves maintained low to moderate FECs. Subsequent to day 12, the following observations were made:

(a) the FEC had decreased to 0 in one animal by day 17;
(b) the FEC had decreased to 0 by day 25 in a further two animals;
(c) the FEC had decreased to 0 in a further animal by day 28;
(d) the FEC had decreased to 0 in a fifth animal by day 35.

A zero FEC was observed at the mean time of 26 days with a standard deviation of 6 days. The observed time for a drop in the FEC from 180 to 300 epg to zero epg, in such animals, is approximately 4 days (data not presented). This data indicates that the mean time of a release of the anthelmintic test formulation from the device was 22 days with a standard deviation of 6 days.

We claim:

1. A controlled release container comprising:

an outer shell, at least a portion of which comprises a biodegradable polymeric material having a predetermined rate of degradation; and a core, enclosed by said outer shell, comprising at least one bioactive molecule as an active ingredient optionally admixed with at least one of a pharmaceutically acceptable carrier, a veterinarily acceptable carrier, and an excipient;

said outer shell being produced separately from said core;

said portion of said outer shell providing a predetermined delay of at least two days after administration of said controlled release container in the time period of release of said active ingredient.

2. A container according to claim 1, wherein said polymeric material degrades when in contact with bodily fluids, said degradation comprising reduction in molecular weight of the polymeric material to a predetermined value during said predetermined delay, wherein said degradation is sufficient to release said active ingredient after said predetermined delay.

3. A container according to claim 1, wherein said predetermined delay is at least four days after administration.

4. A container according to claim 1, wherein said predetermined delay is at least two weeks after administration.

5. A container according to claim 1, wherein said biodegradable polymeric material is selected from a group consisting of a polyester, a polyamide, and a polysaccharide.

6. A container according to claim 1, wherein said biodegradable polymeric material is a polyester selected from a group consisting of polylactide, polylactide-polyglycolide, and polyhydroxybutyrate-polyhydroxyvalerate polyesters.

7. A container according to claim 6, wherein the biodegradable polymeric material is a polylactide-polyglycolide copolymer.

8. A container according to claim 1, wherein the outer shell is formed by melt processing.

9. A container according to claim 8, wherein the outer shell is formed by injection moulding.

10. A container according to claim 1, wherein said portion of said outer shell is non-porous.

11. A container according to claim 1, wherein said polymeric material has an initial molecular weight of less than 200,000 and a molecular weight not exceeding 10,000 after said predetermined delay.

12. A container according to claim 1, wherein said container has a shape selected from a group consisting of elongate, and generally cylindrical.

13. A container according to claim 12, wherein said container is formed as an implant device, or as part of an implant device.

14. A container according to claim 1, wherein said container is in a form of a two-part capsule, wherein a first part is biodegradable, and a second part is nonbiodegradable or biodegradable at a different rate than said first part.

15. A container according to claim 1, wherein said container has a form selected from a group consisting of a capped tube, a cylinder, and a rod, wherein one of the cap, tube, cylinder, and rod is biodegradable and the other is non-biodegradable or biodegradable at a different rate.

16. A container according to claim 1, wherein all of said outer shell comprises said biodegradable polymeric material.

17. A container according to claim 1, wherein the active ingredient in the core enclosed by the outer shell comprises at least one bioactive molecule selected from a group consisting of antigens, antibodies, antitoxins, nucleic acids, vaccines, cytokines, growth promotants, hormones, cancer cell inhibitory molecules, cancer cell inhibitory agents, immune stimulants, immune suppressants, anti-inflammatories, anti-microbial agents including antibiotics, anti-viral agents, anti-parasitic agent, vitamins, tonics, stimulants, minerals, inorganic nutrients, and organic nutrients.

18. An outer shell for a controlled release container, at least a portion of said outer shell comprising a biodegradable polymeric material having a predetermined rate of degradation, said portion of said outer shell providing a predetermined delay of at least two days after administration of said controlled release container in the time period of release of the contents of a core enclosed by said outer shell.

19. An outer shell according to claim 18, wherein said portion of said outer shell is non-porous.

20. A method of administering an active ingredient to a human or other animal in a controlled release regime, which comprises administering to said human or other animal a controlled release container according to any of claims 1 to 17, wherein said core of said container comprises said active ingredient.

21. A method according to claim 20, wherein said container is administered in a manner selected from a group consisting of oral ingestion, intraperitoneal injection, intramuscular injection, subcutaneous injection, and intradermal injection.

22. A method according to claim 21, wherein said container is in the form of an implant device, and is administered subcutaneously.

23. A method according to claim 21, wherein said container is incorporated into a weighted capsule or bolus and is administered orally.

24. A method for producing a controlled release container, comprising the steps of:

(i) producing a hollow outer shell by melt processing, at least a portion of said outer shell comprising a biodegradable polymeric material having a predetermined rate of degradation and providing a predetermined delay of at least two days after administration of said controlled release container in the time period of release of contents of a core enclosed by said outer shell;

(ii) inserting a core into said outer shell, said core comprising at least one bioactive molecule as an active ingredient optionally admixed with at least one of a pharmaceutically acceptable carrier, a veterinarily acceptable carrier, and an excipient; and (iii) sealing said core within said hollow outer shell.

25. A method according to claim 24, wherein said biodegradable polymeric material is selected from a group consisting of a polyester, a polyamide, and a polysaccharide.

26. A method according to claim 25, wherein said biodegradable polymeric material is a polyester selected from the group consisting of polylactide, polylactide-polyglycolide and polyhydroxybutyrate-polyhydroxyvalerate polyesters.

* * * * *